United States Patent
Tanaka et al.

(10) Patent No.: US 6,472,661 B1
(45) Date of Patent: Oct. 29, 2002

(54) MASS SPECTROSCOPE FOR LIQUID CHROMATOGRAPH

(75) Inventors: Yasufumi Tanaka; Yoshitake Yamamoto, both of Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 09/535,207

(22) Filed: Mar. 27, 2000

(30) Foreign Application Priority Data

May 6, 1999 (JP) ............................................ 11-125943

(51) Int. Cl.[7] .......................... H01J 49/00; B01D 59/44
(52) U.S. Cl. ...................... 250/281; 250/282; 250/286; 250/287; 250/288
(58) Field of Search ................................ 250/281, 282, 250/286, 287, 288, 292, 423 R; 324/464

(56) References Cited

U.S. PATENT DOCUMENTS

| | | | |
|---|---|---|---|
| 4,542,293 A | * 9/1985 | Fenn et al. | .................. 250/288 |
| 5,304,797 A | * 4/1994 | Irie et al. | .................... 250/287 |
| 6,005,245 A | * 12/1999 | Sakairi et al. | .............. 250/281 |

* cited by examiner

Primary Examiner—John R. Lee
Assistant Examiner—David A. Vanore
(74) Attorney, Agent, or Firm—Beyer Weaver & Thomas LLP

(57) ABSTRACT

A mass spectrometer for a liquid chromatograph includes an atomization chamber into which a liquid sample from the liquid chromatograph is sprayed to be converted into ions, an intermediate chamber at a reduced inner pressure and a detection chamber containing a mass analyzer. A solvent-removing tube is between the atomization chamber and the intermediate chamber for causing liquid droplets containing these ions to pass through. A deflector with at least one pair of planar electrodes is disposed inside the intermediate chamber and opposite each other sandwiching in between the travel path of the ions. Voltage sources apply a variable DC voltage to the solvent-removing tube and different variable DC voltages to each of the electrodes. Data on voltages to be applied to the solvent-removing tube and to the electrodes for optimizing efficiency with which ions with different mass numbers are received by the mass analyzer are preliminarily obtained by using standard samples and stored in a memory device. A control unit serves to apply a specified voltage to the mass analyzer and simultaneously controls the voltage sources so as to have selected voltages applied to the solvent-removing tube and to the electrodes, according to the data stored in the memory.

6 Claims, 3 Drawing Sheets

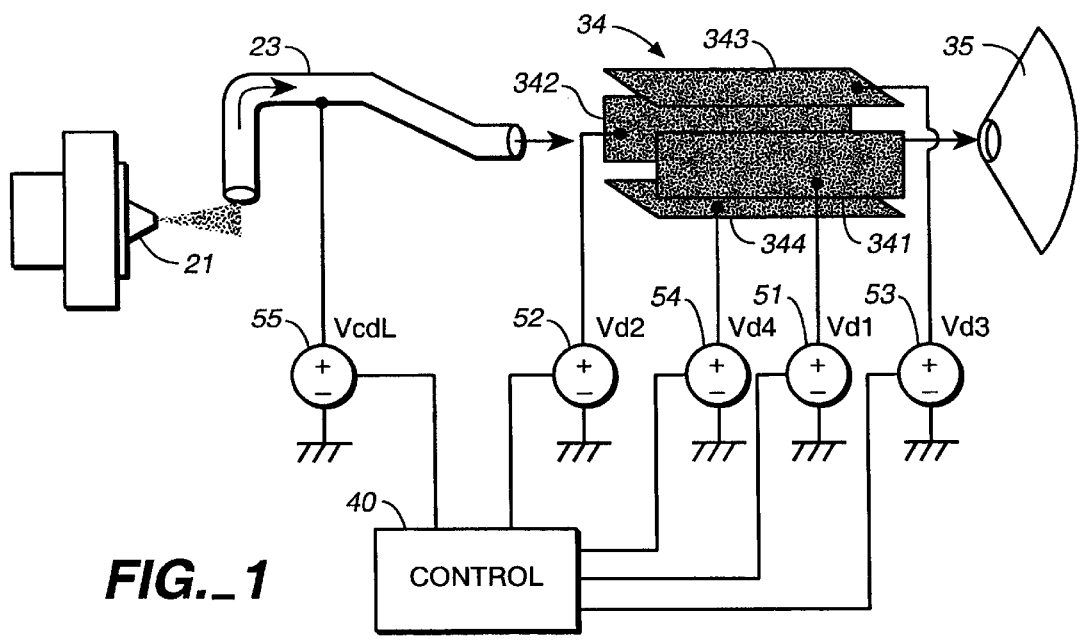
FIG._1
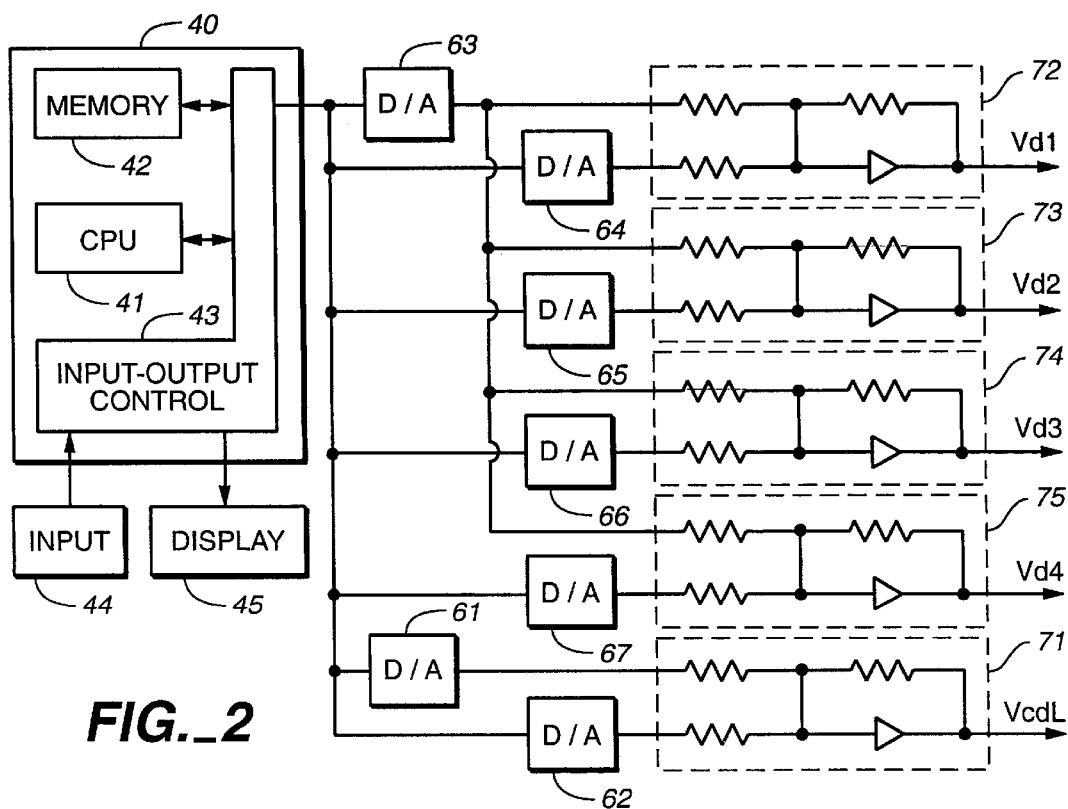
FIG._2

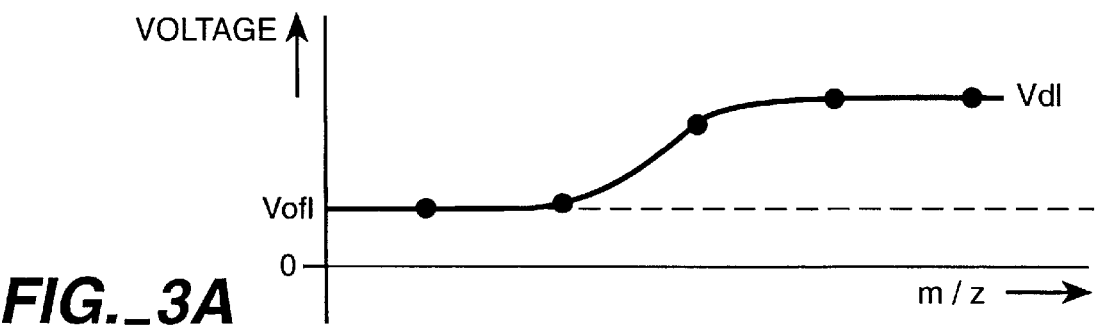
FIG._3A
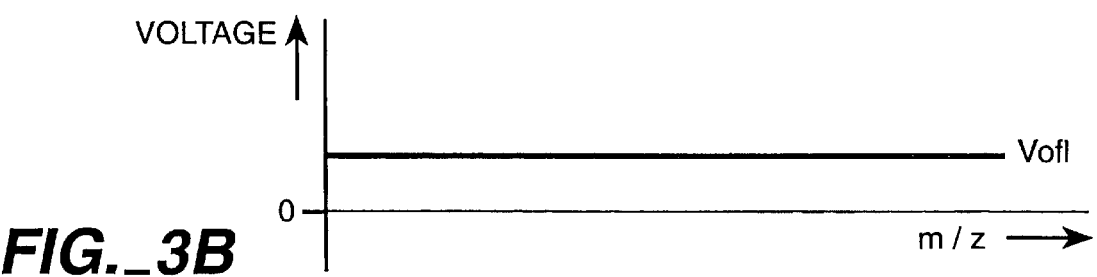
FIG._3B
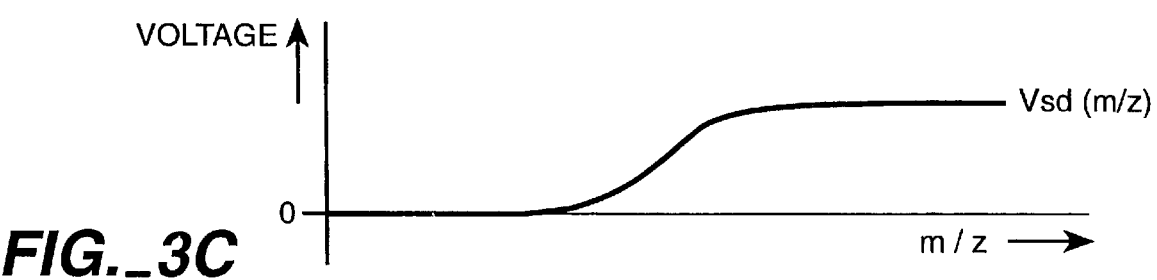
FIG._3C
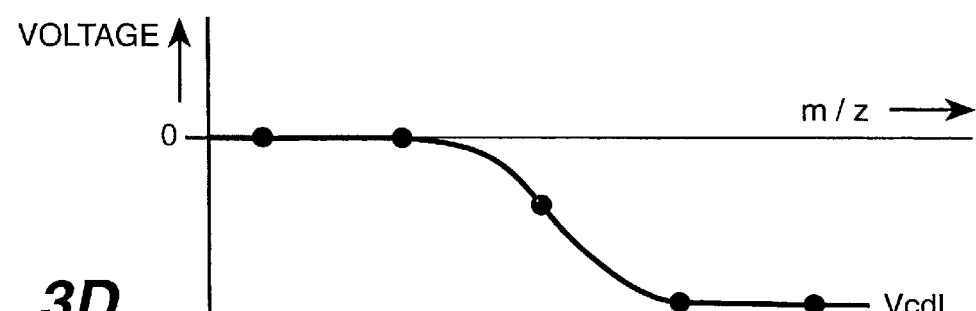
FIG._3D

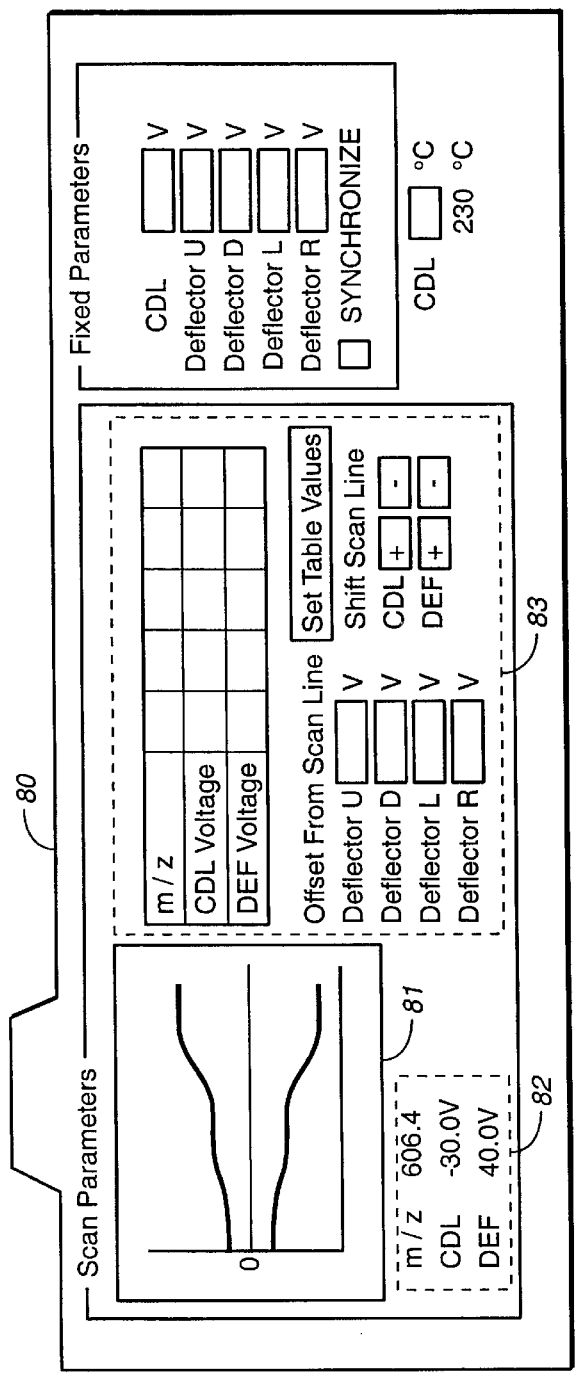
FIG._4
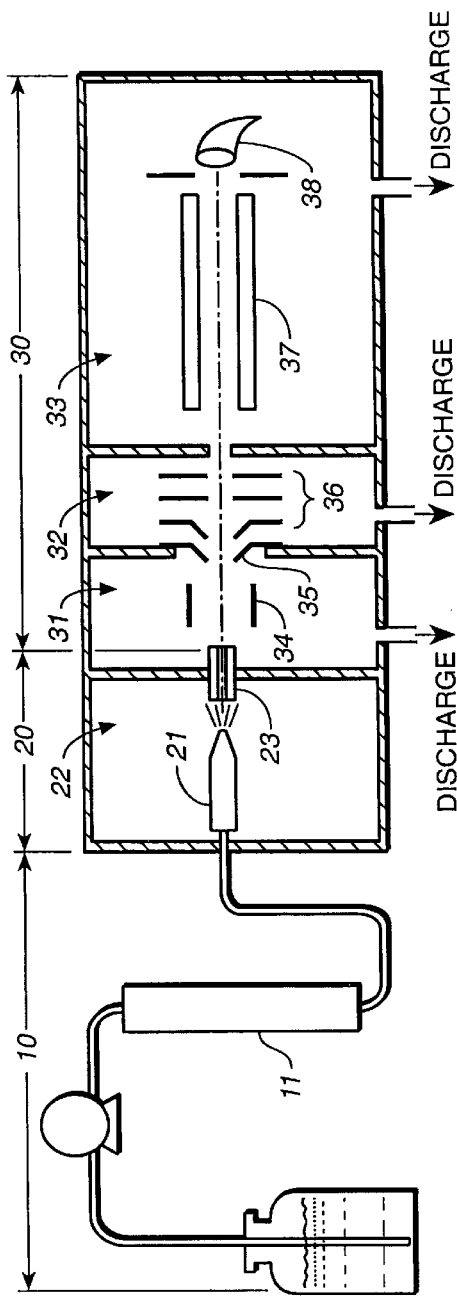
FIG._5
(PRIOR ART)

MASS SPECTROSCOPE FOR LIQUID CHROMATOGRAPH

BACKGROUND OF THE INVENTION

This invention relates to a mass spectroscope used in liquid chromatography, or a mass spectroscope for a liquid chromatograph (herein abbreviated into "LC-MS").

As shown in FIG. 5, a representative example of currently available LC-MS may be described as consisting of a liquid chromatograph (LC) part 10, an interface part 20 and a mass chromatograph (MS) part 30, and a liquid sample which elutes from a column 11 in the LC part 10 in a time-wise separated manner is introduced into the interface part 20 and is sprayed into an atomization chamber 22 through a nozzle 21 to be ionized. The ions thus generated are passed into the MS part 30 through a solvent-removing tube 23 such as a heated capillary. The MS part 30 consists of a first intermediate chamber 31, a second intermediate chamber 32 and an analyzer chamber 33, the solvent-removing tube 23 and a skimmer 35 having an orifice with an extremely small diameter being provided respectively between the atomization chamber 22 and the first intermediate chamber 31 and between the first intermediate chamber 31 and the second intermediate chamber 32. The interior of the atomization chamber 22 is maintained approximately at an atmospheric pressure but the interior of the first intermediate chamber 31 is reduced to about 1 Torr by means of a rotary pump while the interior of the second intermediate chamber 32 and the analyzer chamber 33 is reduced by means of a turbo molecular pump respectively to about $10^{-3}$–$10^{-4}$ Torr and about $10^{-5}$–$10^{-6}$ Torr. In other words, it is so arranged that the degree of vacuity becomes progressively higher from the atomization chamber 22 to the analyzer chamber 33.

The ions which have passed through the solvent-removing tube 23 are caused to converge to the orifice of the skimmer 35 by means of deflector electrodes 34, pass through the skimmer 35 and are introduced into the second intermediate chamber 32. They are then transported into the analyzer chamber 33, being converged and accelerated by ion lenses 36, and only the target ions having a specified mass number (or the ratio between the mass m and its electric charge z) are allowed to pass through a quadrupole filter 37 disposed inside the analyzer chamber 33 and to reach a detector 38 which is adapted to output a current determined by the number of ions which have been received thereby.

The interface part 20 is for generating gas ions by atomizing the liquid sample through heating, a high-speed gas flow or a high electric field. The so-called atmospheric pressure chemical ionization (APCI) and electro-spray ionization (ESI) methods are most commonly used for this purpose. By the APCI method, a needle electrode is disposed in front of the forward end of the nozzle 21 and the ionization process is carried out by causing the drops of the sample liquid atomized by the heating at the nozzle 21 to undergo a chemical reaction with the carrier gas ions (buffer ions) generated by the corona discharge from the needle electrode. By the ESI method, a highly uneven electric field is generated by applying a high voltage of several kV to the tip of the nozzle 21. The liquid sample is separated according to the charge by this electric field and atomization takes place by the Coulomb attraction. The solvent in the liquid drops is evaporated by contacting the environmental air and gas ions are thus generated.

By either of these methods, the generated small liquid drops containing ions are introduced into the heated solvent-removing tube 23 and the evaporation of the solvent inside these liquid drops takes place while these liquid drops are transported into the first intermediate chamber 31. Since the spontaneous destruction of the liquid drops due to the Coulomb repulsion is accelerated as the liquid drops become smaller, the generation of the target ions is also accelerated.

In order to improve the sensitivity of analysis by using an LC-MS thus structured, it is important to ionize the liquid sample efficiently at the interface part 20 and to introduce the generated ions efficiently into the quadrupole filter 37 (or any other kind of mass analyzer). These can be accomplished only if various parameters for the operations of the interface part 20 and the MS part 30 (such as the temperatures and applied voltages) are properly set. With a prior art LC-MS, the voltages to be applied to the solvent-removing tube 23 and the deflector electrodes 34 are adjusted such that the number of ions reaching the detector 38 will be maximized, for example, when a standard sample containing a specified component is introduced, that is, such that the peak of the mass spectrum corresponding to this specified component will reach a highest value. In practice, however, the voltage at which the solvent-removing tube 23 and the deflector electrodes 34 pass the ions most efficiently depends on the mass number of these ions. When a measurement is taken by scanning over a certain range of masses, therefore, the solvent-removing tube 23 and the deflector electrodes 34 are not necessarily in optimum conditions for passing the ions, and this has been one of the factors preventing the prior art LC-MS from operating under an optimum condition in terms of the sensitivity and accuracy of the detection.

SUMMARY OF THE INVENTION

It is therefore an object of this invention in view of these problems to provide an improved mass spectroscope for a liquid chromatograph capable of efficiently introducing target ions to be analyzed into the mass spectroscope part such that its detection sensitivity and detection accuracy can be improved.

A mass spectroscope for a liquid chromatograph embodying this invention, with which the above and other objects can be accomplished, may be characterized not only as comprising an interface including an atomization chamber into which a liquid sample from the liquid chromatograph is sprayed to be converted into ions, an intermediate chamber at a reduced inner pressure and a detection chamber at a lower inner pressure than the intermediate chamber and containing a mass analyzer but also as having a solvent-removing tube for causing liquid droplets containing these ions to pass through from the atomization chamber into the intermediate chamber, means for causing these ions to travel along a travel path through the intermediate chamber into the detection chamber, a deflector having at least one pair of planar electrodes disposed inside the intermediate chamber and opposite each other sandwiching the travel path in between, a voltage generating means for applying a variable DC voltage to the solvent-removing tube, separate voltage generating means for independently applying a different variable DC voltages to each of these electrodes, a memory which stores data on voltages to be applied to the solvent-removing tube and to the electrodes for optimizing efficiency with which ions with different mass numbers are received by the mass analyzer, and a control unit for applying a specified voltage to the mass analyzer and simultaneously controlling the voltage generating means so as to have voltages selected according to the data stored in the memory and applied to the solvent-removing tube and to the electrodes.

In using a mass spectrometer according to this invention, one or more standard samples containing components with different mass numbers are preliminarily analyzed to determine optimum voltages to be applied to the solvent-removing tube and the deflector electrodes for each of the mass numbers. A voltage scan pattern is produced on the basis of these data such that optimum or nearly optimum voltages can be applied corresponding to all mass numbers of interest, and the pattern thus produced is stored in a memory device. At the time of a measurement, the voltages to be applied are varied such that only the ions having particular mass numbers are sequentially allowed to pass through. At the same time, the control unit controls the voltages to be applied according to the pattern stored in the memory such that each group of ions having a particular mass number can pass through the solvent-removing tube and the deflector electrodes under an optimum or nearly optimum condition to be received by the mass analyzer.

Since preferred pattern shapes are empirically known, it is preferable to produce such patterns according to an algorithm, based on separate data which may be obtained by analyzing a plurality of standard samples, as explained above.

BRIEF DESCRIPTION OF THE DRAWINGS

The accompanying drawings, which are incorporated in and form a part of this specification, illustrate an embodiment of the invention and, together with the description, serve to explain the principles of the invention. In the drawings:

FIG. 1 is a schematic structural diagram of a portion of a mass spectroscope for a liquid chromatograph (LC-MS) embodying this invention;

FIG. 2 is a schematic block diagram of the voltage control circuit of the LC-MS of FIG. 1;

FIGS. 3A, 3B, 3C and 3D are voltage scanning patterns for the LC-MS of FIG. 1;

FIG. 4 is an example of a display which may be made on the screen of the display device; and FIG. 5 is a schematic structural diagram of a prior art mass spectrometer for a liquid chromatograph.

DETAILED DESCRIPTION OF THE INVENTION

The invention is described next by way of an example which is generally structured as shown and described above with reference to FIG. 5 but of which the structure between the nozzle 21 and the skimmer 35 is different, as shown schematically and enlarged in FIG. 1.

As shown in FIG. 1, the solvent-removing tube 23 according to this invention is in a bent form such that its inlet opening is approximately perpendicular to the direction in which liquid drops are sprayed through the nozzle 21. This design is adopted for the purpose of preventing relatively large liquid drops and electrically neutral molecules from passing through the solvent-removing tube 23. The deflector electrodes 34 are formed with two mutually oppositely positioned pairs of planar electrodes each in the form of a net, one of the pairs of the electrodes being positioned one (the upper electrode 343) above the other (the lower electrode 344) and the other pair consisting of a right-hand electrode 341 and a left-hand electrode 342 with respect to the travel path of the liquid drops leaving the solvent-removing tube 23. With the electrodes 34 each thus structured in the form of a net, the solvent which has been vaporized from the liquid drops within the space surrounded by these electrodes 34 can be quickly removed through the openings therethrough.

A DC voltage $V_{cdL}$ is applied to the solvent-removing tube 23 through a DC voltage source 55, and DC voltages $V_{d1}$, $V_{d2}$, $V_{d3}$ and $Vd_4$ are independently applied to the four deflector electrodes 341–344 respectively through a different one of four other DC voltage sources 51–54. The DC voltage $V_{cdL}$ may be expressed as the sum of a scan voltage $V_{sc}(m/z)$ which changes according to the mass number (m/z) and a fixed offset voltage $V_{ofs}$ which is independent of the mass number. Similarly, each of the DC voltages $V_{d1}$, $Vd_2$, $V_{d3}$ and $Vd_4$ may be expressed as the sum of a common scan voltage $V_{sd}(m/z)$ which changes according to the mass number (m/z) and an offset voltage $V_{of1}$, $V_{of2}$, $V_{of3}$ or $V_{of4}$ which is independent of the mass number and a constant for each of the four voltages $V_{d1}$, $V_{d2}$, $V_{d3}$ and $Vd_4$. In other words, the DC voltages $V_{cdL}$, $V_{d1}$, $V_{d2}$, $V_{d3}$ and $V_{d4}$ may be written as follows:

$$V_{cdL}=K_1 V_{sc}(m/z)+K_2 V_{ofs},$$

$$V_{d1}=K_1 V_{sd}(m/z)+K_2 V_{of1},$$

$$V_{d2}=K_1 V_{sd}(m/z)+K_2 V_{of2},$$

$$V_{d3}=K_1 V_{sd}(m/z)+K_2 V_{of3},$$

$$V_{d4}=K_1 V_{sd}(m/z)+K_2 V_{of4}.$$

Numeral 40 indicates a control unit for controlling the application of these voltages.

FIG. 2 shows the structure of the control unit 40 as well as the DC voltage sources 51–55. The control unit 40 comprises a multi-purpose personal computer including a CPU 41, a memory 42 and an input-output control 43 and is connected to an input device 44 such as a keyboard and a mouse, a display device 45 such as a CRT and a plurality of digital-to-analog (D/A) converters 61–67 to be described below. The aforementioned DC voltage sources 51–55 include the D/A converters 61–67 for converting digital voltage values outputted from the control unit 40 into an analog voltage, as well as adder-amplifiers 71–75 for adding the scan voltages $V_{sc}(m/z)$ and $V_{sd}(m/z)$ to the offset voltages $V_{of1}$–$V_{ofs}$, as explained above. For example, the DC voltage $V_{d1}$ to be applied to the right-hand deflector electrode 341 is generated by the adder-amplifier 72 which serves to add the scan voltage $V_{sd}(m/z)$ obtained by converting a digital voltage value outputted from the control unit 40 and by the D/A converter 63 and the offset voltage $V_{of1}$ obtained by converting another digital voltage value outputted from the control unit 40 by the D/A converter 64.

Next, the operation of the LC-MS described above will be explained in terms of that of its control unit 40. First, prior to the measurement of an unknown sample, a preparatory measurement is taken by using a standard sample containing a plurality of known components with different mass numbers. The voltage to be applied to the solvent-removing tube 23 and the voltages to be applied to the deflector electrodes 341–344 are determined for this preparatory measurement so as to maximize the heights of the peaks corresponding to these mass numbers in the obtained mass spectrum. On the basis of the relationships thus obtained between the mass numbers and the voltages, the control unit 40 serves to generate a voltage scan pattern for a specified range of mass numbers. Since it is empirically known that the optimum voltage scan pattern for a given range of mass numbers is a curve as shown, for example, in FIG. 3A or 3D, the control unit 40, when a plurality of data are given with mass numbers and voltage values as pairs, employs an algorism to generate a pattern such that a curve as shown above is obtained, including these given data. After a voltage scan pattern is thus formed, corresponding to each of the DC voltages, the scan voltage and the offset voltage are separated as shown in FIGS. 3B and 3C and they are stored in the memory 42 as digital data corresponding to each voltage.

After the scanning of the specified range of mass numbers is started, the control unit 40 controls the voltage to be applied to the quadrupole filter 37 according to factors such as the range of mass numbers and the speed of the scan. In synchronism with this scanning operation, the data which have earlier been stored in the memory 42 are retrieved corresponding to the mass numbers and transmitted to the D/A converters 61–67. The D/A converters 61–67 and the adder-amplifiers 71–75 together serve to apply DC voltages varying as shown in FIGS. 3A and 3D to the solvent-removing tube 23 and the deflector electrodes 341–344 according to the mass scan.

During this voltage scan, those of the ions having a target mass number, out of all the ions generated from the liquid drops sprayed through the nozzle 21, pass through the solvent-removing tube 23 with a particularly high efficiency. Of these ions which have passed through the solvent-removing tube 23 into the space surrounded by the two pairs of deflector electrodes 341–344, furthermore, those having the target mass number are caused to converge into the orifice of the skimmer 35 with a particularly high efficiency and are introduced into the second intermediate chamber 32 on the downstream side. According to the present invention, therefore, an increased number of ions with the target mass number can reach the quadrupole filter 37.

Although the invention has been described above by way of only one example, this example is not intended to limit the scope of the invention. Many modifications and variations are possible within the scope of the invention. Although the voltage scan pattern takes the general form as shown in FIGS. 3A and 3D for any sample, the absolute value of the voltage tends to vary, depending on the sample. The LC-MS embodying this invention, therefore, may be provided with the function of arbitrarily varying the shape of the pattern, based on the one obtained from the measurement of a standard sample.

Explained more in detail, the operator may operate the input device 44 to cause an "adjustment input display" as shown at 80 in FIG. 4 to appear on the screen of the display device 45, including a display of the currently set voltage pattern inside a pattern display frame 81. The user operates a mouse to move a curser on this pattern, causing the mass number and the voltages applied on the solvent-removing tube (CDL) and the four deflector electrodes (DEF) to appear inside a numerical data display frame 82. There is also a number input frame 83 on the display 80 where the user may input numerical voltage values corresponding to each mass number. After the user inputs numbers and then makes a command to set them, the voltage scan pattern changes its shape. These modified voltage scan patterns are also stored in the memory 42 and the voltages thus determined are applied to the solvent-removing tube 23 and the deflector electrodes 34.

It now goes without saying that all such modifications and variations that may be apparent to a person skilled in the art are intended to be within the scope of this invention.

What is claimed is:

1. A mass spectrometer for a liquid chromatograph, said mass spectrometer comprising:

an interface including an atomization chamber into which a liquid sample from said liquid chromatograph is sprayed to be converted into ions, an intermediate chamber at a reduced inner pressure and a detection chamber at a lower inner pressure than said intermediate chamber and containing a mass analyzer;

a solvent-removing tube for causing liquid droplets containing said ions to pass therethrough from said atomization chamber into said intermediate chamber;

means for causing said ions to travel along a travel path through said intermediate chamber into said detection chamber;

a deflector having at least one pair of planar electrodes disposed inside said intermediate chamber and opposite each other sandwiching said travel path therebetween;

a first voltage generating means for applying a variable DC voltage to said solvent-removing tube;

a second voltage generating means for independently applying a different variable DC voltages to each of said electrodes;

a memory storing data on optimum voltages to be applied to said solvent-removing tube and to said electrodes for optimizing efficiency with which ions with different mass numbers are received by said mass analyzer; and a control unit for applying a specified voltage to said mass analyzer and simultaneously controlling said first voltage generating means and said second voltage generating means so as to have selected voltages applied to said solvent-removing tube and to said electrodes, said selected voltages being selected according to said data stored in said memory.

2. The mass spectrometer of claim 1 wherein said solvent-removing tube is bent, having an inlet opening directed perpendicularly to direction of motion of said liquid sample being sprayed into said atomization chamber.

3. The mass spectrometer of claim 1 wherein said deflector has two pairs of planar electrodes disposed facing each other in mutually perpendicular directions which are both perpendicular to said travel path.

4. The mass spectrometer of claim 1 wherein each of said electrodes comprises a net and allows ions and molecules to pass therethrough.

5. The mass spectrometer of claim 1 further comprising a display device and an input device, said display device being controlled by said control unit and displaying a voltage scan pattern according to which specified voltages are applied to said mass analyzer and said input device allowing a user to change shape of said pattern on display device.

6. The mass spectrometer of claim 5 wherein said control unit displays said voltage scan pattern both graphically and numerically.

* * * * *